US012587622B2

(12) United States Patent
Hauger et al.

(10) Patent No.: US 12,587,622 B2
(45) Date of Patent: Mar. 24, 2026

(54) SYSTEM AND METHOD FOR MULTIMODAL IMAGE ACQUISITION AND IMAGE VISUALIZATION

(71) Applicant: CARL ZEISS MEDITEC AG, Jena (DE)

(72) Inventors: Christoph Hauger, Aalen (DE); Tilman Schmoll, Wien (AU); Nancy Hecker-Denschlag, Ulm (DE); Joachim Steffen, Westhausen (DE)

(73) Assignee: CARL ZEISS MEDITEC AG, Jena (DE)

( * ) Notice: Subject to any disclaimer, the term of this patent is extended or adjusted under 35 U.S.C. 154(b) by 193 days.

(21) Appl. No.: 18/366,868

(22) Filed: Aug. 8, 2023

(65) Prior Publication Data

US 2024/0056558 A1 Feb. 15, 2024

(30) Foreign Application Priority Data

Aug. 10, 2022 (DE) ..................... 10 2022 120 201.1

(51) Int. Cl.
*H04N 13/106* (2018.01)
*A61B 90/00* (2016.01)
(Continued)

(52) U.S. Cl.
CPC ........... *H04N 13/106* (2018.05); *A61B 90/20* (2016.02); *H04N 13/239* (2018.05); *A61B 2090/364* (2016.02); *A61B 2090/3735* (2016.02)

(58) Field of Classification Search
CPC .... H04N 13/106; H04N 13/239; A61B 90/20; A61B 2090/364; A61B 2090/3735
See application file for complete search history.

(56) References Cited

U.S. PATENT DOCUMENTS

2011/0181702 A1* 7/2011 Hauger .............. G01B 9/02091
348/46
2017/0055828 A1* 3/2017 Papac .................. A61B 3/0025
(Continued)

FOREIGN PATENT DOCUMENTS

DE 10 2014 111 630 2/2016
EP 3087907 A1 11/2016
(Continued)

OTHER PUBLICATIONS

European Search Report for App. No. 23185048.8, dated Dec. 14, 2023 (18 pages).
(Continued)

*Primary Examiner* — Rowina J Cattungal
(74) *Attorney, Agent, or Firm* — NIXON PEABODY LLP

(57) ABSTRACT

A system and method for multimodal image acquisition and image visualization, including a surgical-microscopic system with an optical unit and an image sensor and designed for acquiring a time-resolved image signal of a selected field of view of a sample. The system includes an OCT system, which is designed to acquire a time-resolved OCT signal of the selected field of view, a display means designed for the time-resolved display of image data and a control unit. The control unit is configured to ascertain video image data corresponding to the acquired image signal and to present them on the display means, to ascertain a time-resolved OCT image, corresponding at least to a portion of the presented video image data, on the basis of the acquired OCT signal, and to present the OCT image on the display means at the position of the portion.

14 Claims, 4 Drawing Sheets

(51) Int. Cl.
    *A61B 90/20*          (2016.01)
    *H04N 13/239*      (2018.01)

(56)               References Cited

U.S. PATENT DOCUMENTS

| | | | |
|---|---|---|---|
| 2017/0135573 A1 | 5/2017 | Charles | |
| 2018/0168737 A1 | 6/2018 | Ren et al. | |
| 2019/0125182 A1* | 5/2019 | Charles | A61F 2/16 |
| 2021/0169324 A1 | 6/2021 | Tripathi et al. | |
| 2021/0248720 A1* | 8/2021 | Ziesche | A61B 90/20 |
| 2022/0117696 A1 | 4/2022 | Shi et al. | |

FOREIGN PATENT DOCUMENTS

| | | |
|---|---|---|
| JP | 2015-083276 A | 4/2015 |
| JP | 2016-209147 A | 12/2016 |
| JP | 2020-501652 A | 1/2020 |
| WO | 2018/109640 A1 | 6/2018 |

OTHER PUBLICATIONS

Japanese Office Action for App. No. 2023-122429, mailed Jul. 30, 2024 (6 pages).
German Office Action for Application No. 10 2022 120 201.1, mailed Apr. 5, 2023 (16 pages).

\* cited by examiner

SYSTEM AND METHOD FOR MULTIMODAL IMAGE ACQUISITION AND IMAGE VISUALIZATION

CROSS-REFERENCE TO RELATED APPLICATIONS

The present application claims priority under 35 U.S.C. § 119 to German Patent Application No. 10 2022 120 201.1, filed Aug. 10, 2022, the contents of which are incorporated by reference herein in their entirety.

SUBJECT MATTER OF THE INVENTION

The present invention relates to a system and to a method for multimodal image acquisition, in particular for the time-resolved image acquisition of an operating site by acquiring image signals by means of video and optical coherence tomography (OCT) and for the optimized presentation of the multimodal image data. The multimodal image data are in particular stereoscopic image data.

TECHNOLOGICAL BACKGROUND

The use of technological aids is part and parcel of modern medicine. By now, imaging methods and robotic systems are used equally as a matter of course in both surgery and diagnostics. In this context, the use of imaging methods allows the presentation and discrimination of various structures in the patient and the image data obtained from the patient can be used advantageously in diagnostics and also in therapeutic and surgical methods.

By way of example, image data from a patient allows not only a surgeon to plan a surgical intervention better, but also assists them in performing the intervention. Robotic visualization systems are used to assist surgeons when performing surgical interventions. Said systems generally comprise at least one camera for recording images of the region to be operated on, with said camera being carried by a stand with an articulated structure. The stand allows the camera to be positioned relative to the subject by way of translational and/or rotational movements in order to capture images of a desired field of view (FOV) of the region to be operated on. In this context, the use of optical stereo cameras allows the acquisition of 3-D image data.

In addition to the acquisition of surface information from a desired field of view, for example on the basis of reflected or back-scattered visible light, methods for acquiring depth information from the field of view have also been developed in the meantime. These methods include optical coherence tomography (OCT), which allows the three-dimensional microscopic imaging of optically transparent and/or reflective objects and hence the recording of volume images of the biological tissue in the observed field of view. Optical coherence tomography (OCT) essentially is an interferometric method using broadband light with a short coherence length.

Systems for acquiring OCT data therefore comprise an interferometer and a broadband light source with a spectral width of more than 1% of the central wavelength.

OCT data can be acquired sequentially or in parallel. By way of example, sequential acquisition of OCT data is implemented by virtue of a low-coherence source light beam being split at a beam splitter into a sample beam and a reference beam; which are sent through two arms of an interferometer; with a movable reference mirror being arranged in the reference beam path and the object to be examined being arranged in the object beam path. A path difference between object beam and reference beam, and hence the measured sample depth, can be set by displacing the reference mirror. The object beam is scanned over the sample in two dimensions by means of a mirror in the object beam path, allowing three-dimensional scanning of the sample as a result.

In the context of such an acquisition of OCT data in the time domain (time domain OCT—TD OCT), the spectral width of the light source $\Delta\lambda$ corresponds to a coherence length $L_c$ of $L_c = \lambda^*/\Delta\lambda$. The axial resolution of an OCT system corresponds to the coherence length $L_c$ of the utilized light and denotes the capability of resolving objects which have a spacing of at least the coherence length along the optical axis. By way of example, a light source in the near infrared range with a central wavelength of 800 nm and a spectral width of 80 nm has a coherence length of 7 μm and an OCT system having such a source consequently has an axial resolution of approximately 1-10 μm. The transverse resolution of an OCT system is determined by the optical unit used in the object beam path, in particular by the object lens focusing the light on the object to be examined.

A sequential acquisition of OCT data is also possible in the frequency domain (frequency domain OCT—FD OCT), with a distinction generally being made between the use of a tunable source (swept source OCT) and the use of a dispersive detector (spectral domain OCT—SD OCT). In swept source OCT, the frequency of the excitation light source, frequently a laser, is tuned, and as a result it is possible to vary a path difference between sample beam and reference beam, and hence the scanned sample depth, even without a displaceable reference mirror. A broadband light source is likewise used in the case of SD OCT, but the detection is preceded by a separation of the frequency components of the interference signal, for example by an optical grating.

Slice and volume data of biological tissue are acquirable by means of OCT, and this can significantly increase the information content for a surgeon. Consequently, an integration of OCT in surgical microscopes is desirable in order to acquire both video data from the surface of a desired field of view and also depth and/or slice images of the field of view. However, the combined presentation of intraoperative OCT imaging and conventional (3D) imaging in surgical microscopes is complex and provides new challenges for the surgeon. While surgical systems have to date been able to supply volumetric OCT images, their recording times have been relatively long and, moreover, rendering has been restricted to postprocessing only for reasons of time and resources. Volume imaging in real-time during the operation therefore has not been possible to date.

However, as OCT technology and the capacity and speed of graphics processors (GPUs) advance, faster OCT methods for intraoperative imaging are becoming available. As a disadvantage, however, the thus possible presentation of OCT volume images in real-time can overwhelm or distract the surgeon, in particular if OCT and conventional video data are presented on different screens or in different screen regions or if switching between the modalities is not readily possible.

The object of the present invention is to overcome or at least reduce the disadvantages of the prior art and to provide an improved system and an improved method for multimodal image acquisition and image visualization.

DESCRIPTION OF THE INVENTION

The object according to the invention is achieved by the subjects of the independent patent claims. Preferred developments are the subject matter of the dependent claims.

A first aspect of the present disclosure relates to a system for multimodal image acquisition and image visualization, in particular for acquiring and visualizing images by means of a medical device, for example a surgical microscope.

The system according to the present disclosure comprises a surgical-microscopic system having an optical unit, in particular for detecting light, for example visible light, reflected or back-scattered from the sample. By way of example, the optical unit comprises an objective lens and an eyepiece; however, it may moreover comprise further components, in particular further lens elements, mirrors, beam splitters and/or the like. The surgical-microscopic system further comprises an image sensor which is designed to acquire a time-resolved image signal of a selected field of view (region of interest—ROI) of a sample. By way of example, the sample is an operating site on a patient, especially an eye in the case of ophthalmological surgeries. However, the sample may also be any other operating site, for example brain tissue in neurosurgery, tissue located in the ENT region in the case of ENT surgery or the gingiva, tartar or dental nerves in the case of dental surgery. The sample may likewise be any other tissue or preparation (in vivo, in vitro or in situ). The field of view is preferably selected by the user.

The system according to the present disclosure further comprises an OCT system. The OCT system preferably comprises a broadband light source, preferably a tunable (swept source) laser, for example a broadband laser, a super continuum laser and/or an ultrashort pulse laser.

In this case, a tunable laser at any given time can be a narrow-bandwidth light source, the central frequency of which however is selectively variable over time, or can be formed from a plurality of narrow-bandwidth light sources. However, any other broadband source can also be used, for example a superluminescent diode, for example in FD-OCT. The OCT system furthermore preferably comprises an interferometer, for example a Michelson, Mach-Zehnder or Koster interferometer. The interferometer preferably comprises a beam splitter for producing (and superposing) sample and reference beams from the light of the broadband source, a reference beam path and a sample beam path. With further preference, the interferometer comprises means for setting an examined sample depth. Depending on the measurement method, this may be a means for producing a path difference (for instance, a mirror displaceable in the reference beam in the case of SD-OCT), a means for separating light of a specific path difference (for instance, an optical grating in the case of FD-OCT) or means for generating light with a specific path difference (for instance, a tunable source in the case of a swept source OCT). The OCT system preferably furthermore comprises a scanning mechanism for the sample beam, in particular for scanning the sample beam in two dimensions over the sample. The scanning mechanism preferably is a scanning mirror but other scanning mechanisms may also be used, for example an optical fibre scanner, a prism scanner, a Palmer scanner or the like. A scanning mechanism is dispensable in the case of an OCT system configured for a full-field OCT. The OCT system is designed to acquire a time-resolved OCT signal of the selected field of view and preferably has a detector for this purpose. By way of example, the detector is a line detector, a two-dimensional detector array, a photodetector, a dispersive detector, a CCD detector and/or a CMOS detector.

The system according to the present disclosure further comprises a display means designed for the time-resolved display of image data. The display means is preferably one or more screens, for example the at least one screen of a surgical microscope, a screen fixedly installed within an operating theatre or a head-mounted display (HMD), for example a pair of video glasses. The screen is preferably a 4K- and/or 8K-capable screen and/or a 3D screen designed for stereoscopic presentation.

The system according to the present disclosure further comprises a control unit which is connected to the surgical-microscopic system, the OCT system and the display means, in particular for one-directional or bidirectional data transfer. The control unit is designed and configured to ascertain video image data corresponding to the acquired time-resolved image signal. In particular, the time-resolved image signal is a multiplicity of signals assigned to surface elements of the sample, which are acquired sequentially or simultaneously for a specific scan of the sample surface, wherein the scan is determined by a scanning mechanism and/or the image sensor. Further, the time-resolved image signal has a clock frequency (image refresh rate), which is determined by the scanning mechanism and/or the image sensor. From this image signal, the control unit produces video image data with a raster (resolution) and an image refresh rate suitable for the presentation on the display means. The control unit is further configured to display the video image data by means of the display means.

The control unit is further configured to ascertain a time-resolved OCT image on the basis of the OCT signal. The OCT signal is an interference signal, with the modulation of the envelope of the interference signal encoding reflection properties of the sample. The scanning mechanism allows the sample to be scanned in two dimensions at a sample depth set by way of the path difference. A clock frequency (image refresh rate) for the time-resolved OCT signal also arises from the utilized scanning mechanism, the utilized means for selecting or producing the path difference, for example an adjustable mirror in the reference beam, an optical grating upstream of the detector or a tunable broadband light source, and the refresh rate of the detector. The control unit determines a time-resolved OCT image on the basis of the OCT signal by calculation, for example by means of volume rendering, ray tracing and/or ray marching. A person skilled in the art is familiar with various methods for producing time-resolved OCT images from time-resolved OCT signals.

In the system according to the present disclosure, the control unit produces the OCT image in such a way that the produced time-resolved OCT image corresponds at least to a portion of the presented video image data. Preferably, an OCT signal is acquired from the entire field of view and an OCT image of at least a part of the field of view is created. Likewise preferably, an OCT signal is acquired from a portion of the field of view and an OCT image of at least a part of the portion of the field of view is created. The local correspondence of video image data and OCT image is ensured according to the invention either by way of the measurement technology used or by image-processing methods. The control unit is further designed to display the time-resolved OCT image on the display means at the position of the portion of the video image data. Preferably, video image data and an OCT image of the entire field of view are created and are each presented on the entire display means. Likewise preferably, an OCT image of a portion of the field of view is produced and displayed on the display means at the position of the video data corresponding to this portion of the field of view. In other words, video image data and OCT images corresponding to the same portion of the sample are presented at the same location of the display means. The system according to the present disclosure consequently enables a seamless integration of video image data and OCT images on the display means, whereby easier viewing of the multimodal image data is enabled for a user. This allows the multimodal image data to be viewed without moving the head or the eyes, which has an advantageous effect on the attentiveness of the surgeon, in particular in the case of imaging during surgical interventions.

In a particularly preferred embodiment of the system according to the present disclosure, the surgical-microscopic system comprises a stereo camera, which is to say is designed for acquiring stereoscopic time-resolved image signals. The stereo camera for this purpose comprises in particular a first image sensor for acquiring a time-resolved first image signal of the field of view and a second image sensor for acquiring a time-resolved second image signal of the field of view. The first image sensor acquires the first image signal preferably along a first optical axis and by means of a first optical unit, in particular a first objective. The second image sensor acquires the second image signal preferably along a second optical axis and by means of a second optical unit, in particular a second objective. The first optical axis and the second optical axis enclose an angle between them. This angle between the optical axes and a working distance between the sample and the objectives determine a stereo angle of the stereoscopic image acquisition. According to this embodiment, the display means is designed for presenting stereoscopic image data, with the stereo angle being decisive for the depth impression during the image visualization on the display means.

With further preference, the control unit of the system according to the invention is configured to produce first video image data corresponding to the first image signal and second video image data corresponding to the second image signal, in each case as described above, and to present them stereoscopically on the display means. The display means is consequently designed to stereoscopically present image data. The display means preferably is a display means designed to display image data with different (e.g., orthogonal) polarizations, in combination with polarization glasses. However, the display means might also be a 3D screen, for example a light-field monitor or the like. The control unit is further configured to ascertain a time-resolved first OCT image and a time-resolved second OCT image from the time-resolved OCT signal that has been acquired. The OCT system consequently offers the possibility of producing stereoscopic image data without the need for stereoscopic signal acquisition. According to this preferred embodiment, the first OCT image corresponds at least to a portion of the presented first video image data and the second OCT image corresponds at least to the same portion of the presented second video image data, in each case as described above. The control unit is furthermore designed to stereoscopically present the first and the second OCT image on the display means at the position of the portion. This yields the advantages according to the invention of optimized multimodal image visualization also as part of a stereoscopic presentation of image data. The control unit preferably takes into account the stereo angle of the surgical-microscopic system during the production of the stereoscopic OCT images. An identical depth impression of the stereoscopic video image data and of the stereoscopic OCT images is advantageously ensured in this way.

In the system according to the present disclosure, an image signal preferably comprises a multiplicity of first tuples. In this case, each first tuple comprises (or represents) a surface element of the sample and at least one greyscale value. In this case, the surface element of the sample is preferably represented by two lateral spatial coordinates (for example x and y) and can be interpreted for example as a sample pixel. In addition to the greyscale value, which ultimately results from a detected intensity, each first tuple may moreover also comprise colour values, for example during the detection of intensities for different colours by means of colour filters connected upstream of the image sensor. Furthermore, an OCT signal comprises a multiplicity of second tuples, which each comprise (or represent) a volume element of the sample and a scattering intensity. In this case, the volume element of the sample is preferably represented by three spatial coordinates (for example x, y and z) and can be interpreted for example as a sample voxel. The second tuple may include further values in addition to the scattering intensity. According to this embodiment, the display means comprises a multiplicity of pixels and the control unit is configured to ascertain the video image data on the basis of the first tuples and on the basis of a resolution of the display means in such a way that specific pixels display specific surface elements of the sample. In other words, the control unit ascertains a first assignment of pixels of the display means and surface elements of the sample. In this case, this assignment may depend on further settings, for example on a zoom level of the surgical-microscopic system, but is preferably constant over time for given settings. The control unit of this embodiment is furthermore configured to ascertain the OCT images from the second tuples and the resolution of the display means and/or the video image data in such a way that volume elements corresponding to the specific surface elements are presented on the specific pixels. In other words, the control unit ascertains a second assignment of pixels of the display means and volume elements of the sample, which corresponds to the first assignment ascertained. Therefore, the control unit realizes spatial registration between pixels of the display means and the image signals (video image data) and also the OCT signals (OCT images).

With further preference, the control unit is configured to locally register the image signals acquired by the surgical-microscopic system and the OCT signals acquired by the OCT system on the basis of acquisition parameters of the OCT system and of the surgical-microscopic system. In this context, a local registration of these signals denotes correct linking of these signals to a reference coordinate system, for example the coordinate system of the patient during an intervention, and enables a unique mapping of coordinates of the patient space onto corresponding coordinates of the signal space. A registration of the signals preferably requires a calibration of the surgical-microscopic system and OCT system. The acquisition parameters of the surgical-microscopic system preferably comprise calibration parameters and/or optical settings of the surgical-microscopic system, for example a focal length and/or a zoom level of an optical unit (camera) utilized. Moreover, the acquisition parameters preferably also comprise a set of intrinsic parameters of the surgical-microscopic system. In this case, the intrinsic parameters determine a relationship between the coordinate system of an image signal and the coordinate system of the associated imaging sensor. In this case, the type of the intrinsic parameters depends in particular on the type of imaging sensor utilized, with imaging sensor in this case denoting both the actual sensor and the utilized optical unit. The intrinsic parameters comprise, for example in the case of Tsai's camera calibration which is known to a person skilled in the art, an effective focal length, the coordinates of a principal image point (centre of the distortion) of an image signal, a first scaling factor and/or a first radial lens error coefficient (distortion coefficient). As an alternative to the aforementioned intrinsic parameters of Tsai's camera calibration, other intrinsic parameters can also be used, for example for Zhang's camera calibration (cf., for example, "*A practical comparison between Zhang's and Tsai's calibration approaches*", Li et al., Proceedings of the 29th International Conference on Image and Vision Computing New Zealand, November 2014 Pages 166-171, DOI: 10.1145/2683405.2683443). The OCT system likewise has acquisition parameters which preferably comprise calibration parameters. The acquisition parameters of the OCT system preferably also take into account the scanning mechanism and/or the detector of the OCT system. Using the local registration on the basis of the acquisition parameters, it is advantageously possible to correctly present structures of the patient situated at defined coordinates of the patient space at the corresponding coordinates in the image space of the video image data and in the image space of the OCT images.

In a likewise preferred embodiment of the system according to the present disclosure, the control unit is alternatively or additionally designed to locally register the video image data and OCT images by means of an image analysis. In this case, a local registration of these image data denotes correct linking of these images in a common image coordinate system. The registration on the basis of the image data consequently allows relative linking of the image data for an image representation of the same structures that is as congruent as possible. By way of example, structure or tissue boundaries can be recognized in the video image data and the OCT images by means of image analysis, for example edge detection or the like, and can be compared to one another. These structures can then be overlaid on one another on the display means by way of a translational displacement, rotation and/or scaling. The local registration of the image data is preferably implemented in addition to a local registration of the acquired signals.

The control unit of the system is preferably configured to simultaneously present the video image data and the time-resolved OCT image on the display means. This particularly advantageously allows the simultaneous consideration of both image modalities by a user. To nevertheless allow a distinction to be made between the different image data, the control unit is further preferably configured to present the video image data with a first level of transparency and the time-resolved OCT image with a second level of transparency. In this case, the first and the second level of transparency preferably differ from one another. The first and the second level of transparency likewise preferably vary over time. By way of example, the image signal is initially presented with a transparency of 0% while the OCT image is presented with a transparency of 100%. Over the course of time, the transparency of the image signal is then adjusted continuously from 0% to 100% while the transparency of the OCT image is simultaneously adjusted from 100% to 0%. This consequently ensures a continuous transition between the presentation of the video image and of the OCT image.

In a likewise preferred embodiment of the system according to the present disclosure, the control unit is configured to present the video image data and the time-resolved OCT image sequentially on the display means. In other words, only one of video image data and OCT images is presented at any one time, at least at a specific location on the display means. This advantageously allows a clear distinction to be made between video image data and OCT data and likewise advantageously allows a simultaneous presentation of the various image data at different locations on the display means.

Particularly preferably, the control unit is configured to present the video image data and the time-resolved OCT image with the same magnification, the same perspective and/or the same stereo angle. In the case of a simultaneous presentation of both video image data at the same location of the display means, this preferably enables a perfect overlay of both image data and may advantageously enable a presentation with an optimized contrast. In the case of a sequential presentation, preferably a presentation with the same magnification, the same perspective and/or the same stereo angle occurs at the transition between the locally registered image data. Consequently, a fluid transition occurs between the presentation of the image data. Only a presentation of the surface (top view) is possible in the case of the video image data. By way of example, this corresponds to an "en face" OCT image. As soon as there has been a transition from video image data to the OCT image, a user can further preferably adapt the magnification, perspective and/or stereo angle in order to advantageously enable an improved view with an optimal depth perception. In particular, a user can switch from the initial "en face" view to a perspective presentation, for example by way of a continuous transition of the viewing direction, or to a slice view (OCT B scan). Consequently, the perfect view is advantageously ensured in various phases.

In the system according to the present disclosure, the time-resolved OCT image preferably corresponds to a portion of the video image data presented. In other words, the OCT image presents merely a portion of the field of view that is viewed by means of the surgical-microscopic system. For example, a time-resolved OCT signal of only a portion of the viewed field of view of the sample may be acquired. In accordance with this preferred embodiment, the control unit is configured to present the OCT image in the portion and to present the video image data on the rest of the display means. By way of example, the video image data and the OCT image are displayed overall simultaneously on the display means but sequentially at the specific locations on the display means. This advantageously enables a display over the entire sample or an entire operating region by means of the video image data, while at the same time a section or detail, for example the region of intervention of a surgical instrument, is presented by means of the OCT images. Since the OCT images also enable a perspective presentation, this embodiment advantageously also enables the combination of a top view in the video image data with the perspective OCT view.

In a particularly preferred embodiment the system according to the present disclosure further comprises an interface for acquiring a user input. The interface is preferably a hand switch or a foot switch. Likewise preferably, the interface is a means for recognizing a head movement and/or eye movement, for example integrated into video glasses or into a head-mounted display, HMD. The interface may further be designed to capture voice commands and may comprise at least one microphone to this end. Likewise preferably, the interface is a keyboard, a joystick, a mouse, a touchscreen or a combination thereof. According to this embodiment, the control unit is configured to initiate a switch in the presentation from video image data to OCT image, or from OCT image to video image data, on the basis of an acquired user input.

In a likewise particularly preferred embodiment of the system according to the present disclosure, the latter further comprises a medical instrument. By way of example, the medical instrument is a probe, a pointer, a pair of tweezers, an awl, a phaco tip, an endoscope, an endo LED or the like.

According to this embodiment, the control unit is further configured to determine a position, a type and/or a state of the medical instrument. In this case, a type of the medical instrument can be implemented preferably on the basis of an interface for connecting the medical instrument and/or on the basis of an input via a user interface. Likewise preferably, a type of the medical instrument introduced into the field of view of the surgical-microscopic system is identified by an image analysis of the video image data, for example by means of segmentation and object recognition. A position of the medical instrument is preferably ascertained on the basis of the detection of a marker, wherein the marker may be a label on or a structure of the medical instrument. The marker is preferably detected by means of the surgical-microscopic system and optionally using additional light sources (e.g. infrared LEDs) and/or following a registration/calibration of the medical instrument (e.g. by positioning a tip of the medical instrument at a defined location).

A state of the medical instrument introduced into the field of view of the surgical-microscopic system is likewise preferably determined on the basis of an image analysis of the video image data. By way of example, whether tweezers are opened or closed can be identified on the basis of the image data. Moreover, a user input for changing a state can be read by the control unit; for example, a user input for activating a phaco tip signals a change in the state thereof.

Further, a sensor attached to the medical instrument can detect a change in the state of the latter, for example tweezers being closed, and can transmit a corresponding sensor signal to the control unit.

According to this preferred embodiment, the control unit is further configured to initiate a switch in the presentation from video image data to time-resolved OCT image, or from the time-resolved OCT image to video image data, on the basis of the position, the type and/or the state of the medical instrument. A change in the state of a medical instrument of a specific type and/or at a specific location is preferably indicative of a specific phase of an operation. Consequently, recognizing the position, the type and/or the state of the medical instrument can be used to choose the optimal form of presentation for this phase. This comprises not only the switching of the image data, but optionally also a change of presentation parameters within the image data, for example a zoom level, a stereo angle, a viewing direction, a presented depth and/or a cut direction.

Likewise preferably, the control unit is configured to ascertain a zoom level of the surgical-microscopic system and to initiate a switch of the presentation of video image data and of the time-resolved OCT image on the basis of the zoom level. As a rule, a small zoom value corresponds to a large field of view, with a presentation of details generally not being desired. Therefore, it is preferably concluded on the basis of a small zoom level that no presentation of OCT images is desired. By contrast, a large zoom value corresponds to a small field of view, in which a detailed presentation is frequently desired. Therefore, it is preferably concluded on the basis of a small zoom level that a presentation of OCT images is desired.

Further preferably, the control unit is configured to ascertain a phase of a performed operation. To this end, the control unit is preferably connected to a memory in which a trained machine learning algorithm, for example a neural network (CNN) or the like, is stored. This algorithm was preferably trained by means of a multiplicity of video image data and/or OCT images or image signals and/or OCT signals, which were assigned a corresponding phase of an operation as a classification during the training. Accordingly, the trained algorithm is able to independently recognize a phase of an operation as a classification on the basis of video image data and/or OCT images or image signals and/or OCT signals. The control unit according to this embodiment is preferably designed to initiate a switch in the presentation from video image data to OCT image, or from the OCT image to video image data, on the basis of the ascertained phase of the operation. The image data which are suitable for different phases of the operation are preferably stored in a memory.

In the case of a cataract operation, the operation phases may for example comprise: rest state, incision, injection of the ophthalmic viscosurgical device (OVD), capsulorhexis, hydrodissection, phacoemulsification, rinse/aspiration, implantation of the intraocular lens, close/moisturize the wound, non-operation. In the case of a refractive operation, the operation phases may for example comprise: Idling, docking, applanation, application of the eye/CG rotation, lens cut, lens side cut, flap cut, flap side cut, uncover the eye, transition to the surgical microscope, positioning of the surgical microscope, open the incision, define the planes, sever the flap bed, sever the lens bed, remove and/or inspect the lenses, wipe, rinse, slit lamp, remove the speculum. In the case of the dental intervention, the surgical phases may for example comprise: access, extirpation, debridement, drying, obturation, restoration. It should be noted that all or only some of these phases may be part of the corresponding operation and that further operation phases may also be present and/or some phases may be omitted.

The functionalities of the control unit according to the invention can be implemented by electrical or electronic devices or components (hardware), by firmware (ASIC) and/or can be realized by carrying out a suitable program (software). Preferably, the functionalities of the control unit according to the invention are realized or implemented by a combination of hardware, firmware and/or software. By way of example, individual components of the control unit according to the invention for carrying out individual functionalities are in the form of a separately integrated circuit or are arranged on a common integrated circuit.

The individual functionalities of the control unit according to the invention are further preferably in the form of one or more processes which run on one or more processors in one or more electronic computers and which are generated when carrying out one or more computer programs. In this case, the control unit is designed to cooperate with the other components, in particular the surgical-microscopic system, the OCT system and the display means, in order to realize the functionalities of the system according to the invention as described herein. It is further evident to a person skilled in the art that the functionalities of a plurality of computers (data-processing devices, control units, controllers) can be combined or can be combined in a single device, or that the functionality of a specific data-processing device may be distributed over a multiplicity of devices in order to realize the functionalities of the control unit according to the invention.

In a particularly preferred embodiment of the system according to the invention, the latter is integrated in a surgical microscope. In this case, the surgical microscope preferably comprises a surgical-microscopic system and an OCT system, in each case as described above. Further preferably, the surgical microscope comprises, or is connected to, a display means. The image sensor and optical unit are preferably part of a camera, in particular of a main observer camera or a surround camera of the surgical microscope. The control unit of the surgical microscope is preferably designed as a control unit of the system according to the invention and, in particular, is designed to carry out the method according to the invention, as described below, on the basis of commands stored on a storage unit of the surgical microscope.

Within the scope of the present disclosure, a surgical microscope is understood to mean in the broadest sense a microscope suitable for use during an operation. The surgical microscope preferably comprises a mount which allows imaging of the operating region independently of head movements of the surgeon. Further preferably, the surgical microscope comprises at least one beam splitter and at least two eyepieces. Alternatively, the surgical microscope is a pure "digiscope" without eyepieces. Likewise preferably, the surgical microscope comprises at least one imaging sensor. Further preferably, the surgical microscope comprises a main observer camera and a surround camera. The surgical microscope may comprise kinematic or robotic aids for carrying out surgical interventions. As an alternative, a surgical microscope may be referred to as a medical engineering microscope, a medically approved microscope or a medical microscope.

A further aspect of the present disclosure relates to a method for multimodal image acquisition and image visualization. The latter includes the method step of acquiring a time-resolved image signal of a selected field of view of a sample by means of a surgical-microscopic system. In this case, the image signal comprises a multiplicity of first tuples, which each represent a surface element of the sample and at least one greyscale value corresponding to the surface element. The method further includes the step of acquiring a time-resolved OCT signal of the selected field of view by means of an OCT system. In this case, the OCT signal comprises a multiplicity of second tuples, which each represent a volume element of the sample and a scattering intensity corresponding to the volume element. The method furthermore includes the step of ascertaining video image data, wherein the video image data are ascertained on the basis of the first tuples and on the basis of a resolution of a display means with a multiplicity of pixels in such a way that pixels determined in the video image data are assigned to specific surface elements of the sample. The method furthermore involves the step of ascertaining a time-resolved OCT image on the basis of the second tuples and on the basis of the resolution of the display means and/or on the basis of the video image data. In the OCT images, volume elements corresponding to the specific surface elements are assigned here to the specific pixels. Consequently, the OCT image corresponds at least to a portion of the video image data. The method furthermore involves the step of presenting the video image data on the display means and presenting the OCT image on the display means, specifically at the position of the portion on the display means. The method according to the present disclosure realizes the same advantages as the system according to the present disclosure, and, in this respect, reference is made to the explanations given above.

In a preferred implementation of the method according to the present disclosure, the latter further includes the step of acquiring a time-resolved first image signal of the field of view and a time-resolved second image signal of the field of view. This acquisition takes place preferably by means of a stereo camera or another camera designed for acquiring stereoscopic image signals. The preferred implementation of the method further involves ascertaining first video image data corresponding to the first image signal and ascertaining second video image data corresponding to the second image signal, which is to say stereoscopic video image data. The step of ascertaining a time-resolved first OCT image which corresponds at least to a portion of the first video image data takes place on the basis of the OCT signal, in particular on the basis of the second tuples and on the basis of the resolution of the display means and/or on the basis of the video image data. Furthermore, the step of ascertaining a time-resolved second OCT image which corresponds at least to the portion of the second video image data takes place on the basis of the OCT signal, in particular on the basis of the second tuples and on the basis of the resolution of the display means and/or on the basis of the video image data. According to this implementation, the stereoscopic presentation of the first video image data, of the second video image data, of the time-resolved first OCT image and of the time-resolved second OCT image on the display means is furthermore effected with the same magnification, the same perspective and/or the same stereo angle. The method according to this implementation advantageously enables the stereoscopic, simultaneous or sequential presentation of video image data and OCT images at the same location of a display means.

Further preferred implementations of the method according to the present disclosure correspond to further preferred embodiments of the system according to the present disclosure and realize the same advantages as the embodiments.

A further aspect of the present disclosure relates to a computer program comprising commands which, when executed by a control unit as described above, preferably of a surgical microscope as described above, cause the system or surgical microscope as described above to carry out the method according to the invention as described above. The computer program preferably comprises commands which, when executed by a control unit as described above, preferably of a surgical microscope, cause the system or surgical microscope as described above to carry out the method according to the invention in accordance with one of the preferred implementations, as described above. In this case, the computer program according to the invention is preferably stored in a volatile memory, for example a RAM element, or in a non-volatile storage medium, for example a CD-ROM, a flash memory or the like.

Further preferred embodiments of the invention will become clear from the other features set out in the dependent claims and from the figures explained below. The various embodiments of the invention that are set forth in this application can advantageously be combined with one another, unless specifically stated otherwise.

DESCRIPTION OF THE FIGURES

The invention will be explained below in exemplary embodiments with reference to the associated drawings, in which:

FIG. 1 shows a schematic illustration of a system 100 for the multimodal image acquisition and image visualization according to a first embodiment.

Figure 1:
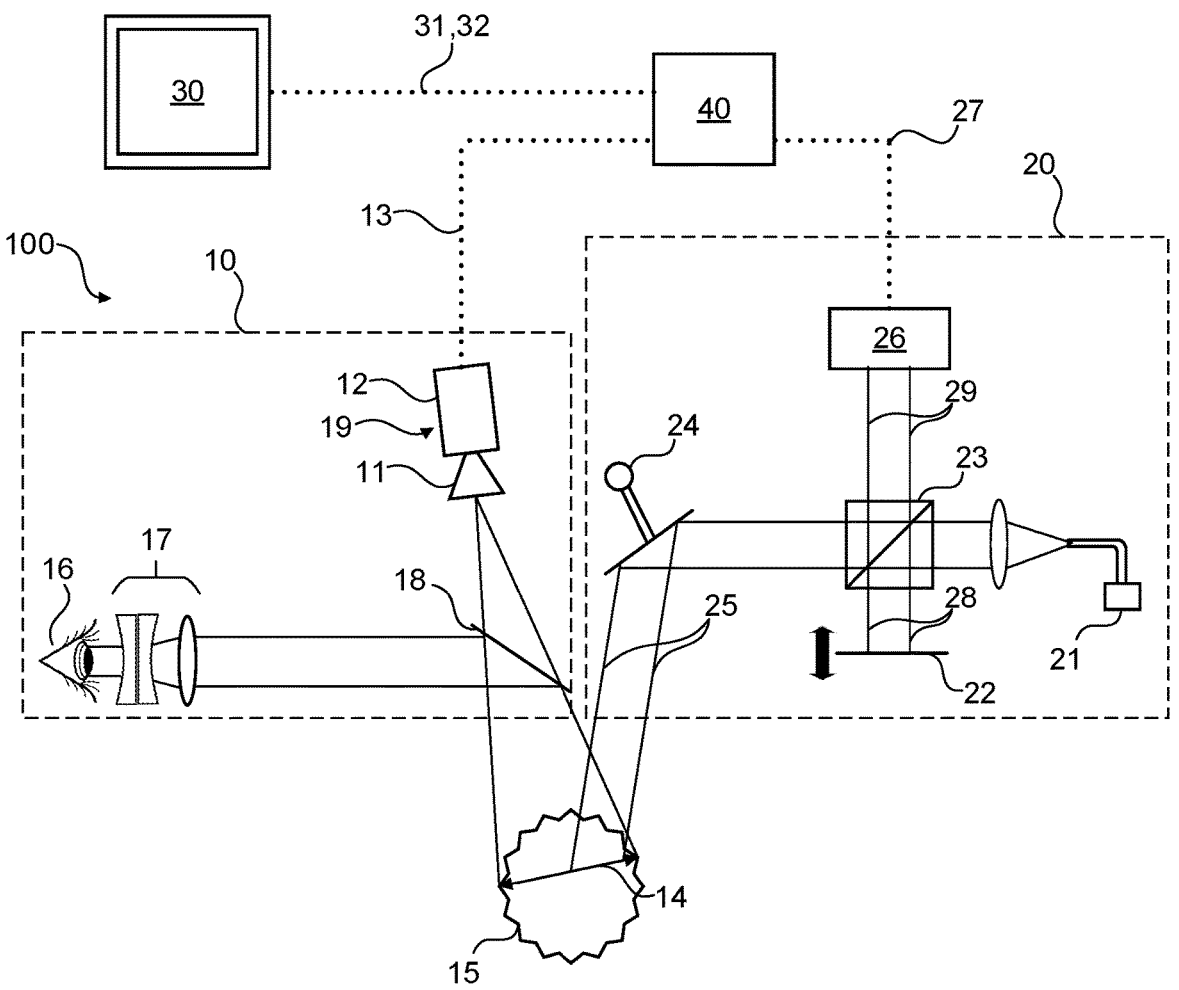
FIG. 1 shows a schematic illustration of a system according to a first embodiment.

The system 100 comprises a surgical-microscopic system 10 with a camera 19 having an optical unit 11 and an image sensor 12. The camera is designed for acquiring a time-resolved image signal 13 of a selected field of view 14 of a sample 15. The camera 19 is, for example, a main observer camera of a surgical microscope which can additionally comprise a surround camera. Likewise, the surgical microscope can comprise an additional beam path which is produced by means of the beam splitter 18 and can be observed through an eyepiece 17 by the eye of a viewer 16. The sample 15 is in particular an operating region of a patient.

The system 100 furthermore comprises an OCT system 20 with a broadband light source 21, for example a superluminescent diode. The light from the light source 21 is fed into an interferometer comprising a movable mirror 22 and a beam splitter 23. The light is split into a sample beam 25 and a reference beam 28 in the interferometer. The sample beam 25 is scanned over the sample 15 by means of a scanning mirror 24, with at least a portion of the field of view 14 of the sample 15 being scanned. The reference beam 28 is steered to the movable mirror 22 and reflected thereby back to the beam splitter 23. The sample beam 25 interacts with the sample 15, in particular with the volume of the sample 15, and is scattered back thereby to the scanning mirror 24, which steers the beam to the beam splitter 23. The back-scattered sample beam 25 and the reflected reference beam 28 are superposed there, with a path difference between the superposed beams 25, 28 being set by the movable mirror 22. The interference pattern 29 thus produced is captured by means of a detector 26, for example a CCD detector or a CMOS detector.

The time-resolved OCT signal 27 thus acquired is transmitted from the detector 26 to the control unit 40, which likewise receives the time-resolved image signal 13 from the camera 19. The control unit 40 ascertains video image data 31 corresponding to the acquired image signal 13 and an OCT image 32 which corresponds to the acquired time-resolved OCT signal 27 and corresponds to at least a portion of the video image data 31. The control unit 40 is configured to present the video image data 31 on the display means 30 which is designed for the time-resolved display of image data 31, 32. The control unit is further designed to display the OCT image 32 on the display means 30 at the position of the at least corresponding portion 60 of the video image data 31. For an explanation, reference is made to the image of FIG. 3.

Figure 3:
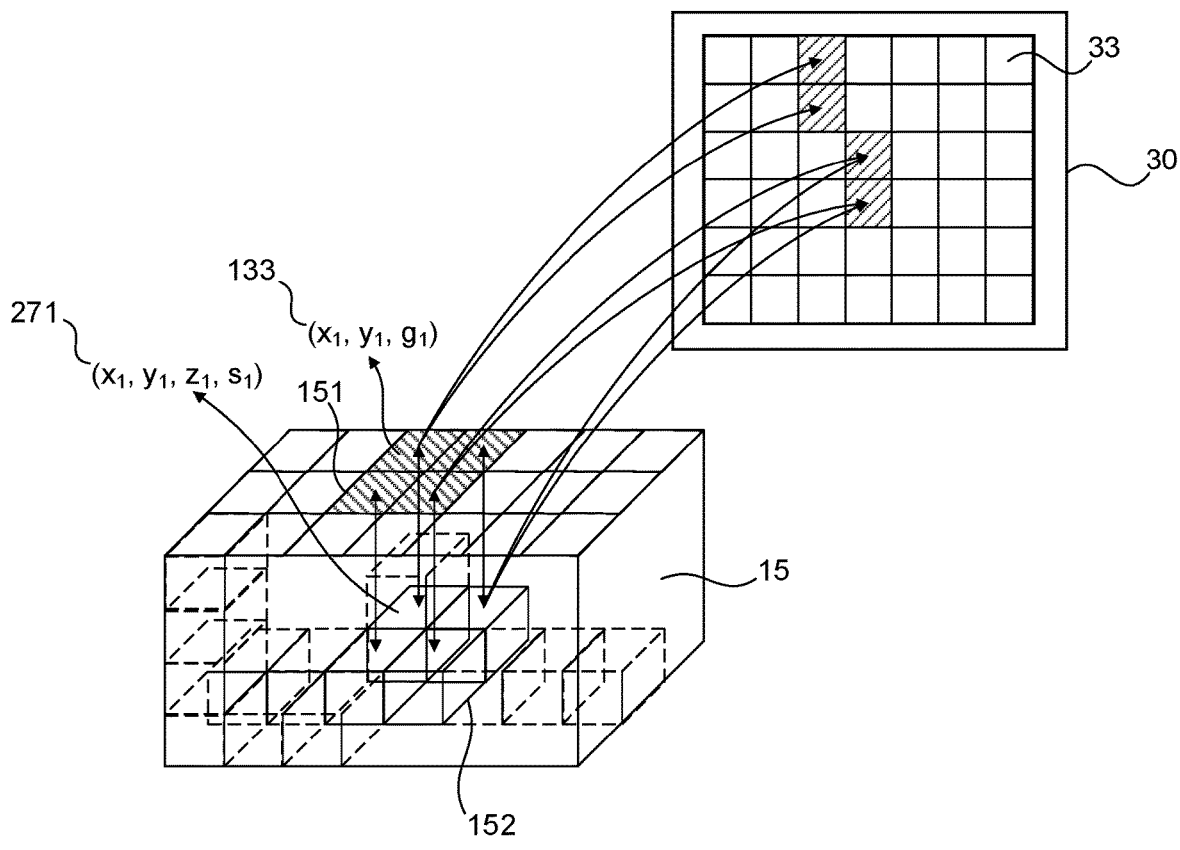
FIG. 3 shows a schematic illustration of a sample and of a display means according to a third embodiment.

FIG. 3 shows a schematic illustration of a sample 15 and a display means 30 according to a third embodiment. In this case, the sample 15 comprises a multiplicity of surface elements 151 and a multiplicity of volume elements 152, with specific volume elements 152 corresponding to specific surface elements 151. An exemplary selection of surface elements 151 is depicted with hatching and while the plurality of the volume elements 152 are depicted using dashed lines, the four volume elements 152 corresponding to the hatched surface elements 151 are depicted using solid lines. Further, double-headed arrows connect these volume elements 152 to the associated surface elements 151.

The surface of the sample 15, in particular, is capturable using the surgical-microscopic system 10 of the system 100 by virtue of long-wavelength (visible) light reflected or scattered back from said surface being cast back to the image sensor 12 of the camera via the optical unit 11. The image signal 13 acquired by means of the image sensor 12 comprises a multiplicity of first tuples 133, with a number of the first tuples 133 arising for example from a resolution of the image sensor 12. Here, each of the first tuples 133 corresponds to one of the presented surface elements 151 and has a greyscale value $g_i$ corresponding to an intensity of the light cast back to the image sensor 12. Furthermore, each of the first tuples 133 is assigned two lateral spatial coordinates $x_i$, $y_i$ on the basis of a calibration or registration of the image sensor 12 relative to a coordinate system of the sample 15 (patient). In the illustrated example, a first tuple 133 has the lateral spatial coordinates $x_1$, $y_1$ and the greyscale value $g_1$.

The OCT system 20 of the system 100 can be used to acquire in particular the volume of the sample 15 by virtue of short-wavelength light of the sample beam 25 scattered thereby being superposed via the scanning mirror 24 on the reference beam 28 by means of the interferometer. The interference pattern thus produced, which is captured by means of the detector 26 as a time-resolved OCT signal 27, comprises a multiplicity of second tuples 271, with a number of the second tuples 271 for example arising from a number of the points on the sample 15 scanned using the scanning mirror 24. In this case, each of the second tuples 271 corresponds to one of the presented volume elements 152 and has a value of a scattering intensity $s_i$. Further, each of the second tuples 271 is assigned three spatial coordinates $x_i$, $y_i$, $z_i$ on the basis of a calibration or registration of the OCT system 20 relative to a coordinate system of the sample 15 (patient). In the illustrated example, a second tuple 271 has the spatial coordinates $x_1$, $y_1$, $z_1$ and the scatter intensity value $s_1$.

The display means 30 also depicted in FIG. 3 comprises a multiplicity of pixels 33, in particular 42 pixels, with 7 pixels in the horizontal direction and 6 pixels in the vertical direction. In the illustrated example, the resolution of the image sensor 12 yielded an acquisition of the sample surface by way of the image signal 13 in 21 surface elements 151 with 7 surface elements 151 in the horizontal direction and 3 surface elements 151 in the vertical direction. Thus, in the video image data 31, one pixel 33 corresponds to one surface element 151 in the horizontal direction and two pixels 33 correspond to one surface 151 in the vertical direction. Pixels 33 corresponding to the surface elements 151 depicted with hatching are likewise depicted with hatching and the assignment is further illustrated by arrows. As is likewise depicted by arrows, the control unit 40 of the system 100 also produces the associated OCT image 32 of the volume elements 152 corresponding to the surface elements 151 and depicts the OCT image in the respective pixels 33 such that video image data 31 of specific surface elements 151 are depicted on specific pixels 33 and OCT images 32 of volume elements 152 corresponding to the surface elements 151 are likewise depicted on the specific pixels 33. Consequently, corresponding video image data 31 and OCT images 32 are depicted at the same location of the display means 30.

Figure 2:
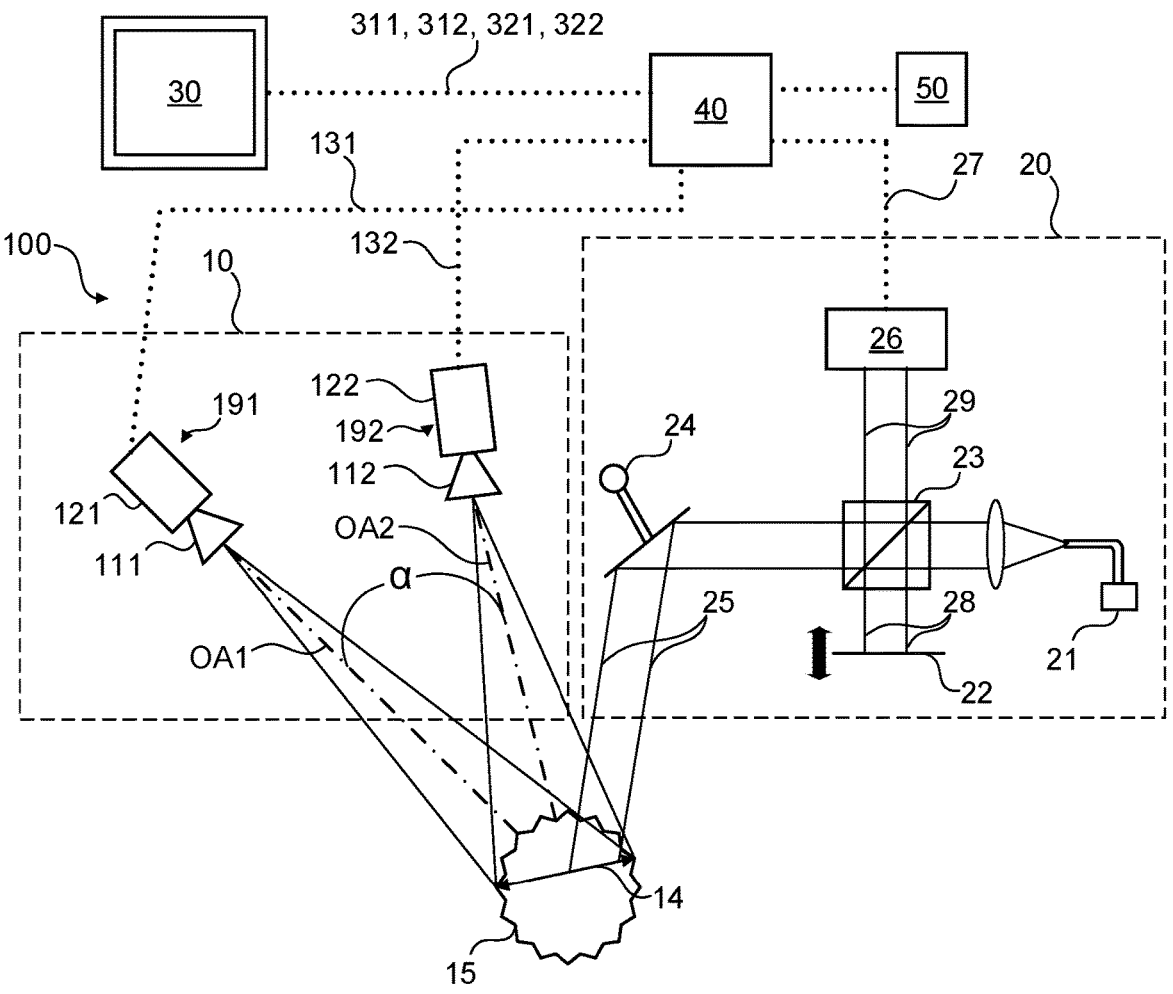
FIG. 2 shows a schematic illustration of a system according to a second embodiment.

FIG. 2 shows a schematic illustration of a system 100 for the multimodal image acquisition and image visualization according to a second embodiment. The same components are denoted by the same reference signs as in FIG. 1 and a repeated description of these components is omitted for reasons of conciseness.

The system 100 in FIG. 2 differs from that in FIG. 1 in that the surgical-microscopic system 10 comprises a first camera 191 with a first optical unit 111 and a first image sensor 121, and a second camera 192 with a second optical unit 112 and a second image sensor 122. Each of these cameras 191, 192 can be used to acquire a field of view 14 of the sample 15 along an optical axis, with the result that a stereoscopic image signal is acquired, with the latter having a first image signal 131 and a second image signal 132. A stereo angle α between the optical axes OA1, OA2 of the two cameras defines a depth impression or a depth perception of the stereoscopic video image data 31 created on the basis of the stereoscopic image signal 131, 132. In this case, the stereoscopic video image data 311, 312 comprise first video image data 311 corresponding to the first image signal 131 and second video image data 312 corresponding to the second image signal 132. In addition to the spacing of the cameras, the stereo angle α depends on a working distance between the cameras and the sample 15.

In the system 100 of FIG. 2, a time-resolved OCT signal 27 is acquired in the same manner, as has already been described with reference to FIG. 1. However, the control unit 40 uses the OCT signal 27 to ascertain a first OCT image 321 corresponding to the first video image data 311 and a second OCT image 322 corresponding to the second video image data 311. In this case, the first OCT image 321 and the second OCT image 322 are for example produced as if they were acquired at the same stereo angle α as the first and second image signals 131, 132. However, a stereo angle of the OCT images 321, 322 can likewise also be set differently on the basis of a user input acquired by means of the interface 50 The first and second video image data 311, 312 are presented simultaneously or sequentially on the display means 30 together with the first and second OCT images 321, 322, wherein a change between the OCT images 321, 322 and the video image data 311, 312 is implemented on the basis of an input by means of the interface 50, for example.

Figure 4:
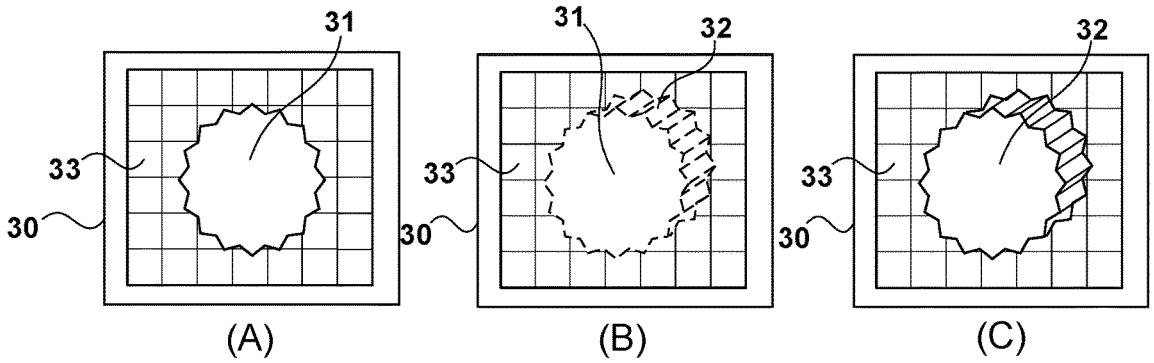
FIG. 4 shows a schematic illustration of a display means according to a fourth embodiment.

A schematic illustration of a display means 30 according to a fourth embodiment is shown in FIG. 4. FIG. 4(A) shows the presentation of video image data corresponding to the sample 15 on pixels 33 of the display means 30, as explained with reference to FIG. 3. From a user input, in particular made by way of the interface 50, for example a foot switch, the control unit 40 gathers that a switch from the video image data 31 to the OCT image 32 of the sample 15 is desired. In the process, the control unit 40 successively increases the transparency of the video image data 31 while at the same time superimposing the corresponding OCT image 32 with decreasing transparency at the location of the video image data 31 on the display means 30. An intermediate stage with a simultaneous and overlaid presentation of semi-transparent video image data 31 and semi-transparent OCT image 32 is shown in FIG. 4(B). Lastly, FIG. 4(C) then only shows the OCT image 32 with a transparency of 0%, i.e. fully covering.

Figure 5:
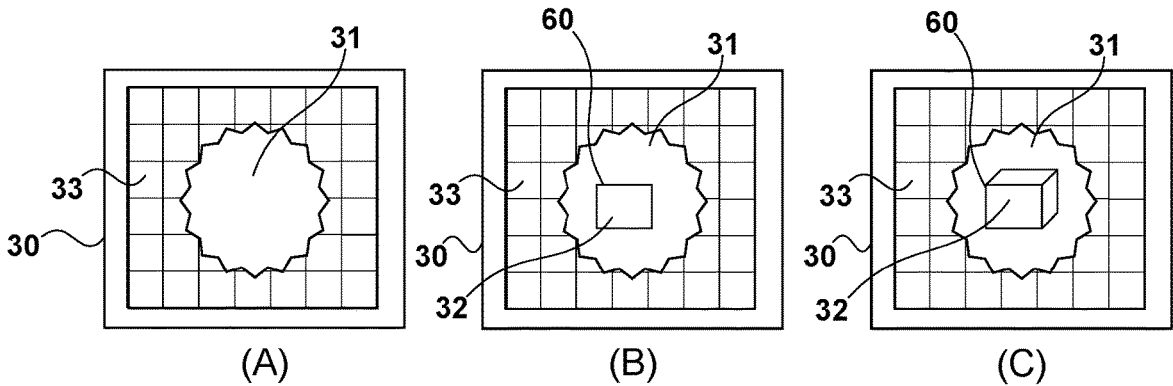
FIG. 5 shows a schematic illustration of a display means according to a fifth embodiment.

A schematic illustration of a display means 30 according to a fifth embodiment is shown in FIG. 5. FIG. 5(A) shows the presentation of video image data corresponding to the sample 15 on pixels 33 of the display means 30 as explained with reference to FIG. 3. From a user input, in particular made by way of the interface 50, for example a sensor for detecting head and eye movements, the control unit 40 gathers that a switch from the video image data 31 to the OCT image 32 of the sample 15 is desired at a specific location of the presentation. The control unit 40 consequently ascertains an OCT image 32 corresponding to the portion 60 of the video image data 31 and displays the OCT image 32 on the display means 30 at the position of the portion 60. In the process, the OCT image 32 is presented initially in an "en face" presentation in order to ensure a seamless transition to the video image data 31 captured in top view. From a further user input made by means of the interface 50, the control unit 40 subsequently gathers that the presentation of the OCT image 32 of the portion 60 is desired in a perspective presentation and therefore modifies a viewing direction of the OCT image 32 so that it is presented, as shown in FIG. 4(C), as a perspective volume image. Therefore, no more video image data 31 are displayed at the location of the OCT image 32, and in this respect the display of the OCT image 32 and video image data 31 is sequential. However, video image data 31 continue to be displayed in the region of the display means 30 surrounding the OCT image 32, and in this respect the display of the image data 31, 32 takes place simultaneously.

Figure 6:
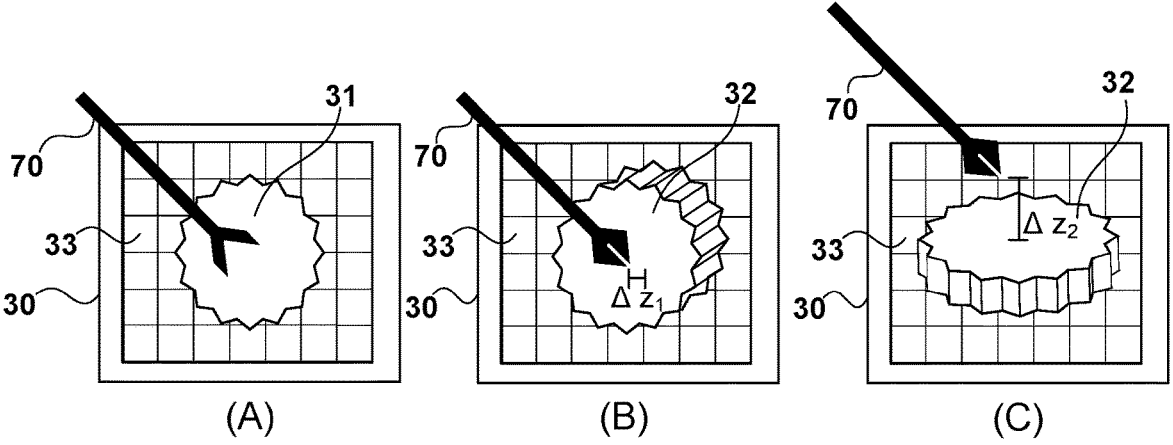
FIG. 6 shows a schematic illustration of a display means and of a medical instrument according to a fifth embodiment.

A schematic illustration of a display means 30 according to a sixth embodiment is shown in FIG. 6. In this case, the system 100, as shown in FIG. 2, further comprises a medical instrument 70, in particular tweezers 70. In a phase where the tweezers 70 approach the sample 15, shown in FIG. 6(A), the open tweezers 70 and the sample 15 are presented on the display means 30 in the form of video image data 31, as explained with reference to FIG. 3. As soon as the control unit 40 recognizes, on the basis of sensor values and/or on the basis of the video image data 31, that the tweezers 70 are closed and a vertical distance between a tip of the tweezers 70 and a surface of the sample 15 is equal to or less than a predetermined limit value $\Delta z_1$, the control unit 40 changes the presentation of the sample 15 and optionally of the tweezers 70 on the display means 30 from the video image data 31 to the OCT image 32, as shown in FIG. 6(B). In the illustrated example, the tweezers 70 are used to lift or remove a part of the surface of the sample 15. As soon as the control unit 40 recognizes, on the basis of sensor values and/or on the basis of the video image data 31, that the tweezers 70 are closed and a vertical distance between a tip of the tweezers 70 and a surface of the sample 15 away from the lifted or removed surface of the sample 15 (e.g., laterally spaced apart by a minimum value) is equal to or greater than a predetermined limit value $\Delta z_2$, the control unit 40 additionally changes the viewing direction or perspective of the presentation of the OCT image 32, with the result that it is now displayed on the display means 30 in a lateral perspective as a volume image, as is shown in FIG. 6(C). In this way, an interaction between the surgeon and the surgical microscope is continuously and objectively improved by the advantageous presentation of the acquired signals, in particular of the image signal 13 and the OCT signal 27, be it through free choice of the locally registered presented image data, i.e. video image data 31 or OCT image 32, and/or through the choice of the manner of presentation, for example in a sequential, simultaneous and/or perspective manner.

Figure 7:
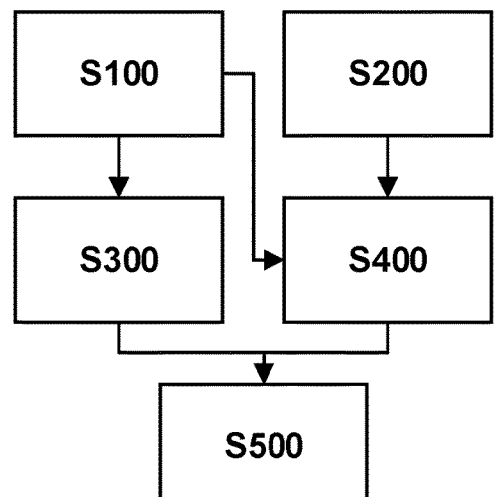
FIG. 7 shows a schematic flowchart of a method according to an implementation.

FIG. 7 shows a schematic flowchart of a method according to an implementation. The method includes a first method step S100 of acquiring a time-resolved image signal 13 of a selected field of view 14 of a sample 15 by means of a surgical-microscopic system 10. In this case, the image signal 13 comprises a multiplicity of first tuples 133, which each represent a surface element 151 of the sample 15 and at least one greyscale value corresponding to the surface element 151. In a second step S200 of the method, a time-resolved OCT signal 27 of the selected field of view 14 is acquired by means of an OCT system 20. In this case, the OCT signal 27 comprises a multiplicity of second tuples 271, which each represent a volume element 152 of the sample 15 and a scattering intensity corresponding to the volume element 152. In a step S300, video image data 31 are ascertained on the basis of the first tuples 133 and on the basis of a resolution of a display means 30 with a multiplicity of pixels 33, wherein specific pixels 133 in the video image data 31 are assigned to specific surface elements 151. In a step S400, a time-resolved OCT image 32 is ascertained on the basis of the second tuples 271 and on the basis of the resolution of the display means 30 and/or on the basis of the video image data 31. This is shown in FIG. 7 by the two arrows pointing at step S400, although only one of the arrows needs to be realized. In this case, volume elements 152 corresponding to the specific surface elements 151 are assigned to the specific pixels 33 such that the OCT image 32 corresponds at least to a portion 60 of the video image data 31. Lastly, in step S500, the video image data 31 are presented on the display means 30 and the OCT image 32 is presented on the display means 30 at the position of the portion 60.

LIST OF REFERENCE SIGNS

10 Surgical-microscopic system
11 Optical unit
111 First optical unit
112 Second optical unit
12 Image sensor
121 First image sensor
122 Second image sensor
13 Time-resolved image signal
131 First image signal
132 Second image signal
133 First tuples
14 Field of view
15 Sample
151 Surface element
152 Volume element
16 Eye of a viewer
17 Eyepiece
18 Beam splitter
19 Camera
191 First camera
192 Second camera
OA1 First optical axis
OA2 Second optical axis
20 OCT system
21 Broadband light source
22 Movable mirror (interferometer)
23 Beam splitter (interferometer)
24 Scanning mechanism (scanning mirror)
25 Sample beam
26 Detector
27 Time-resolved OCT signal
271 Second tuples
28 Reference beam
29 Interference signal
30 Display means
31 Video image data
311 First video image data
312 Second video image data
32 OCT image
321 First OCT image
322 Second OCT image
33 Pixel
40 Control unit
50 User interface
60 Portion
70 Medical instrument

The invention claimed is:

1. A method for multimodal image acquisition and image visualization, comprising the method steps of:
    acquiring a time-resolved image signal of a selected field of view of a sample by means of a surgical-microscopic system, wherein the image signal comprises a multiplicity of first tuples which each represent a surface element of the sample and at least one greyscale value corresponding to the surface element;
    acquiring a time-resolved optical coherence topography (OCT) signal of the selected field of view by means of an OCT system, wherein the OCT signal comprises a multiplicity of second tuples which each represent a volume element of the sample and a scattering intensity corresponding to the volume element;
    ascertaining video image data on the basis of the first tuples and of a resolution of a display means with a multiplicity of pixels, wherein specific pixels in the video image data are assigned to specific surface elements;
    ascertaining a time-resolved OCT image on the basis of the second tuples and of the resolution of the display means and/or of the video image data, wherein the volume elements corresponding to the specific surface elements are assigned to the specific pixels such that the time-resolved OCT image corresponds at least to a portion of the video image data;
    presenting the video image data on the display means and presenting the time-resolved OCT image on the display means at the position of the portion, wherein the video image data is overlaid with the time-resolved OCT image.

2. The method according to claim 1, further comprising the method steps of:
    acquiring a time-resolved first image signal of the field of view and a time-resolved second image signal of the field of view;
    ascertaining first video image data corresponding to the first image signal and second video image data corresponding to the second image signal;
    ascertaining a time-resolved first OCT image, corresponding at least to a portion of the first video image data, and a time-resolved second OCT image, corresponding at least to the portion of the second video image data;
    stereoscopically presenting the first video image data, the second video image data, the time-resolved first OCT image and the time-resolved second OCT image on the display means with the same magnification, the same perspective and/or the same stereo angle α.

3. The method according to claim 2, wherein the surgical-microscopic system comprises a stereo camera with a first image sensor for acquiring the time-resolved first image signal of the field of view and with a second image sensor for acquiring the time-resolved second image signal of the field of view, and the display means is designed to present stereoscopic image data.

4. The method according to claim 2, wherein
    the first and the second OCT images are stereoscopically presented on the display means at the position of the portion.

5. The method according to claim 1, wherein the image signals and OCT signals are locally registered on the basis of acquisition parameters of the OCT system and of the surgical-microscopic system, and/or video image data and OCT images are locally registered by means of image analysis.

6. The method according to claim 1, wherein the video image data and the time-resolved OCT image are presented simultaneously on the display means.

7. The method according to claim 6, wherein the video image data are presented with a first level of transparency and the time-resolved OCT image is presented with a second level of transparency.

8. The method according to claim 1, wherein the video image data and the time-resolved OCT image are presented sequentially on the display means.

9. The method according to claim 1, wherein the time-resolved OCT image corresponds to a portion of the presented video image data, and the OCT image is presented in the portion and the video image data are presented on the rest of the display means.

10. The method according to claim 1, wherein a switch in the presentation of video image data and of the time-resolved OCT image is initiated on the basis of a user input acquired by means of an interface for acquiring a user input.

11. A system for multimodal image acquisition and image visualization, comprising:

a surgical-microscopic system with an optical unit and an image sensor, which is designed for acquiring a time-resolved image signal of a selected field of view of a sample, wherein the image signal comprises a multiplicity of first tuples which each represent a surface element of the sample and at least one greyscale value;

an optical coherence topography (OCT) system designed to acquire a time-resolved OCT signal of the selected field of view, wherein the OCT signal comprises a multiplicity of second tuples which each represent a volume element of the sample and a scattering intensity;

a display means designed for the time-resolved display of image data with a multiplicity of pixels; and a control unit, which is configured to ascertain video image data corresponding to the acquired image signal and to present them on the display means, wherein the video image data are ascertained on the basis of the first tuples and of a resolution of the display means in a manner such that specific pixels display specific surface elements, to ascertain a time-resolved OCT image, corresponding at least to a portion of the presented video image data, on the basis of the acquired OCT signal and to present the time-resolved OCT image on the display means at the position of the portion, wherein the time-resolved OCT image is ascertained on the basis of the second tuples and of the resolution of the display means and/or of the video image data in a manner such that the volume elements corresponding to the specific surface elements are presented on the specific pixels, and wherein the video image data is overlaid with the time-resolved OCT image.

12. The system according to claim 11, further comprising a medical instrument, wherein the control unit is configured to ascertain a position, a type and/or a state of the medical instrument and to initiate a switch in the presentation of video image data and of the time-resolved OCT image on the basis of the position, the type and/or the state of the medical instrument.

13. The system according to claim 11, wherein the control unit is configured to ascertain a zoom level of the surgical-microscopic system and/or to ascertain a phase of a performed operation and to initiate a change in the presentation of video image data and of the time-resolved OCT image on the basis of the zoom level and/or the phase.

14. A system comprising:

a computer-readable storage medium having stored thereon machine-readable commands; and a control unit having one or more processors configured to execute the machine-readable commands to cause the system to carry out the method according to claim 1.

\* \* \* \* \*